(12) United States Patent
Prescott

(10) Patent No.: US 6,387,703 B1
(45) Date of Patent: May 14, 2002

(54) METHOD FOR MODULATING GENE EXPRESSION

(75) Inventor: Catherine D Prescott, Cambridge (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/529,095

(22) PCT Filed: Oct. 7, 1998

(86) PCT No.: PCT/US98/21052

§ 371 Date: Apr. 6, 2000

§ 102(e) Date: Apr. 6, 2000

(87) PCT Pub. No.: WO99/18116

PCT Pub. Date: Apr. 15, 1999

Related U.S. Application Data

(60) Provisional application No. 60/061,218, filed on Oct. 7, 1997.

(51) Int. Cl.$^7$ ................................................. C12N 15/63

(52) U.S. Cl. ............................................ 435/471; 435/6

(58) Field of Search ..................... 435/471, 6; 536/24.5

(56) References Cited

U.S. PATENT DOCUMENTS

| 4,777,129 A | * 10/1988 | Dattagupta et al. ............. 435/6 |
| 5,298,422 A | 3/1994 | Schwartz et al. ......... 435/320.1 |
| 5,616,459 A | * 4/1997 | Kramer et al. .................. 435/5 |
| 5,663,064 A | 9/1997 | Burke et al. ............. 435/172.3 |

OTHER PUBLICATIONS

Tang, et al., "Rational design of allosteric ribozymes," *Chemistry & Biology*, 4(6): 452–459 (1997).

* cited by examiner

*Primary Examiner*—Remy Yucel
*Assistant Examiner*—Bronwen M. Loeb
(74) *Attorney, Agent, or Firm*—Jason C. Fedon; Edward R. Gimmi; Charles M. Kinzig

(57) ABSTRACT

This invention relates to a method of screening for compounds that modulate gene expression, particularly those which lower gene expression.

13 Claims, 1 Drawing Sheet

SEQUENCE LISTING

<160> NUMBER OF SEQ ID NOS: 3

<210> SEQ ID NO 1
<211> LENGTH: 38
<212> TYPE: RNA
<213> ORGANISM: Homo sapiens
<220> FEATURE:
<221> NAME/KEY: unsure
<222> LOCATION: (15)(16)(17)(18)
<223> OTHER INFORMATION: Wherein n can be re presented by a, c, g, or u

<400> SEQUENCE: 1 ggucagccc uaggnnnncc uagguaagca auggaccc           38

<210> SEQ ID NO 2
<211> LENGTH: 14
<212> TYPE: RNA
<213> ORGANISM: Homo sapiens
<220> FEATURE:
<221> NAME/KEY: unsure
<222> LOCATION: (1)(2)(3)(4)(5)(9)(10)(11)(12)(13)(14)
<223> OTHER INFORMATION: Wherein n can be re presented by a, c, g, or u

<400> SEQUENCE: 2
nnnnnagcnn nnnn           14

<210> SEQ ID NO 3
<211> LENGTH: 19
<212> TYPE: RNA
<213> ORGANISM: Homo sapiens
<220> FEATURE:
<221> NAME/KEY: unsure
<222> LOCATION: (1)(2)(3)(4)(5)(6)(15)(16)(17)(18)(19)
<223> OTHER INFORMATION: Wherein n can be re presented by a, c, g, or u

<400> SEQUENCE: 3
nnnnnnuaag caaunnnnn           19

METHOD FOR MODULATING GENE EXPRESSION

This is a 371 of International Application PCT/US98/21052, filed Oct. 07, 1998, which claims benefit of U.S. Provisional Application Serial No. 60/061,218, filed Oct. 07, 1997 expire.

FIELD OF THE INVENTION

This invention relates to a method of screening for compounds that modulate gene expression, particularly those which lower gene expression, and compositions useful in such methods.

BACKGROUND OF THE INVENTION

Methods are known which lower or abolish gene expression. For example, gene knockouts may be performed to abolish gene expression. Conditional lethal mutants may also be created to abolish gene expression and identify essential genes (see, for example, de Lorenzo, V. et al., *Gene* 123:17–24 (1993); Neuwald, A. F. et al., *Gene* 125: 69–73 (1993); and Takiff, H. E. et al., *J. Bacteriol.* 174:1544–1553 (1992). Chemical mutagenesis is yet another way to make such mutants Beckwith, J., *Methods in Enzymology* 204: 3–18(1991). Ribozymes provide another way to lower gene expression levels by damaging the gene or transcript. It has also been reported that the hammerhead RZ with abasic residues can be activated by addition of the base in trans. A drawback to these methods of preparing gene knockouts or lowering gene expression is that they are often time consuming and difficult to reproduce.

A SELEX generated RNA aptamer that binds malachite green has been reported. This complex, when illuminated at 630 nm, results in cleavage of the RNA by free radical generation as shown by abolishing marker gene activity.

The present invention provides improved methods for modulating, lowering and/or abolishing gene expression in a sequence-directed manner.

Various changes and modifications within the spirit and scope of the disclosed invention will become readily apparent to those skilled in the art from reading the following descriptions and from reading the other parts of the present disclosure.

SUMMARY OF THE INVENTION

The invention provides a method for modulating gene expression comprising the steps of: selecting a polynucleotide binding agent binding site and polynucleotide binding agent; contacting an organism with the binding site and binding agent; and detecting modulation of gene expression.

The invention also provides a preferred method, wherein after the contacting step the binding site and binding agent enter the cell and contact an RNA target or DNA target.

A further preferred method comprises the step of having the binding site base pair with an RNA target molecule.

The invention also provides a method wherein the modulation of gene expression is lowering or inhibiting gene expression.

Moreover, the invention provides a method wherein the binding site is selected from the group consisting of a site that binds: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donors, DEANO, spermine NONOate, S-nitrosoglutathione, SNAP, SIN-1, M-7904, 2-hydroxyacetophenone oxime and Fenton's reagent.

Further, the invention provides a method wherein the binding site is selected from the group consisting of a site that: binds a metal ion, creates a coordination complex with a metal ion or other atom or molecule, and is an iron response element.

Also provided is a method wherein the polynucleotide binding agent is selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donors, DEANO, spermine NONOate, S-nitrosoglutathione, SNAP, SIN-1, M-7904, 2-hydroxyacetophenone oxime and Fenton's reagent.

A method is also provided for altering the structure of a polynucleotide comprising the steps of: selecting a polynucleotide binding agent binding site and polynucleotide binding agent; contacting a polynucleotide with the binding site and binding agent; and detecting an alteration in the structure of the polynucleotide.

A method is provided wherein the alteration in the structure is a cleavage of the polynucleotide phosphate backbone.

Another method is provided for modulating the function of a polynucleotide comprising the steps of: selecting a polynucleotide binding agent binding site and polynucleotide binding agent; contacting a polynucleotide with the binding site and binding agent; and detecting modulation of the function.

The invention provides a method for modulating gene expression comprising the steps of: selecting a polynucleotide binding agent binding site and polynucleotide binding agent; contacting an organism with the binding site and binding agent; irradiating the binding agent with electromagnetic radiation; and detecting modulation of gene expression.

A preferred method is also provided wherein the contacting step also comprises contacting the binding site agent with a metal ion, metal salt or metal oxide.

Another preferred method is provided wherein the polynucleotide binding agent is malachite green and the electromagnetic radiation has a wavelength of about 630 nanometers (herein "nm").

A kit is provide by the invention comprising at least on compartment containing an isolated polynucleotide binding agent binding site and a polynucleotide binding agent.

A preferred embodiment of the invention is a kit wherein the polynucleotide binding agent is selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donors, DEANO, spermine NONOate, S-nitrosoglutathione, SNAP, SIN-1, M-7904, 2-hydroxyacetophenone oxime and Fenton's reagent.

Another preferred embodiment of the invention is a kit wherein the polynucleotide binding agent is malachite green.

GLOSSARY

The following definitions are provided to facilitate understanding of certain terms used frequently herein.

"Host cell" is a cell which has been transformed or transfected, or is capable of transformation or transfection by an exogenous polynucleotide sequence and includes, but is not limited to organisms as defined elsewhere herein.

"Flanking sequence" is a polynucleotide sequence on either side (5' or 3') of and fused to the PBA binding site that is complementary, in whole or part to a polynucleotide sequence in the target polynucleotide.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chiamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigellaflexneri, Pseudomonas aeruginosa, Franscisella tularensis, Brucella abortis, Bacillus anthracis, Bacillus cereus, Clostridium pegrfingens, Clostridium tetani, Clostridium botulinum, Treponema pallidum, Rickettsia rickettsii* and *Chlamydia trachomitis*, (ii) an archaeon, including but not limited to Achaebacter, and (iii) a unicellular or filamentous eukaryote, including but not limited to, a protozoan, a fungus, a member of the genus Saccharomyces, Kiuveromyces, or Candida, Coccidiodes, Histoplasma, Cryptococcus and Paracoccidioides.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"PBA binding site" herein means a polynucleotide that binds a PBA and/or a target polynucleotide.

"Polynucleotide Binding Agent" and "PBA" herein means an element or compound that binds to a polynucleotide.

"Target polynucleotide" as the term is used herein, is a polynucleotide selected for structural or functional alteration.

DETAILED DESCRIPTION OF THE INVENTION

Figure 1:
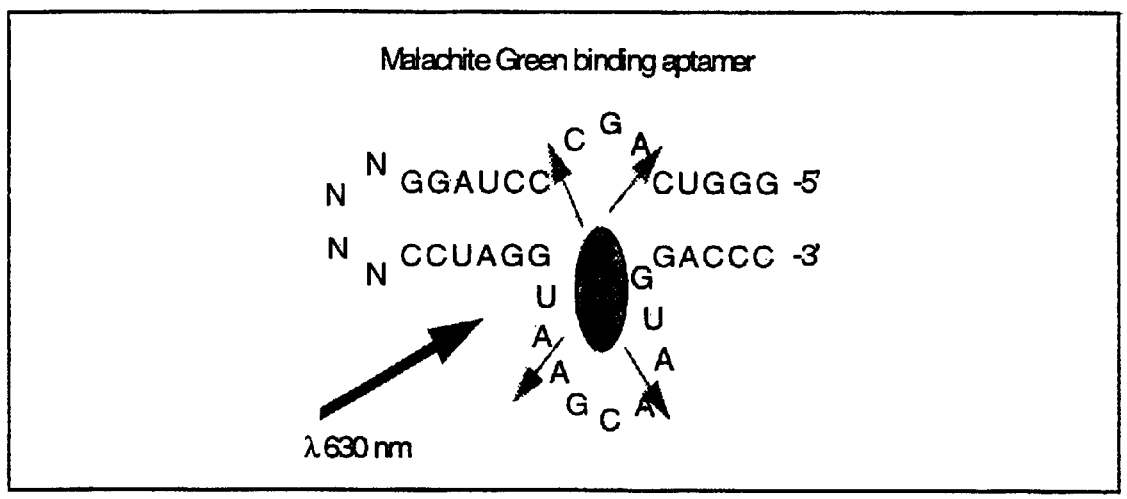
FIG. 1 (top panel) shows an example of purative model of a malachite green binding aptamer (SEQ ID NO:1). The lower panel shows an example of a putative model of a PBA binding site (SEQ. ID NOS:2 and 3) that binds malachite green (SEQ ID NO:2).
Figure 1:
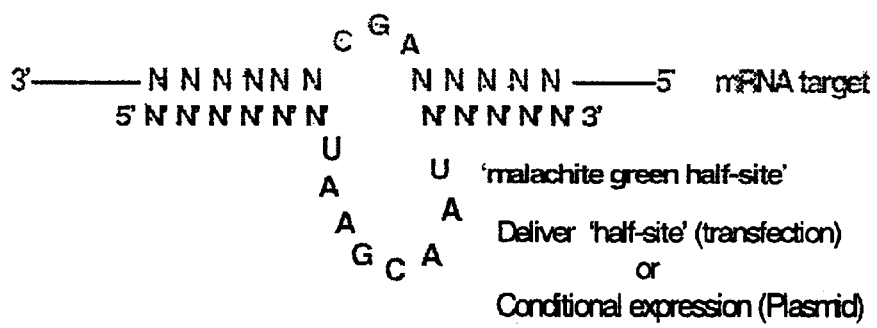

The present invention provides novel methods and compositions useful for lowering and/or abolishing gene expression. The invention provides methods comprising small polynucleotide molecules that bind to a target polynucleotide and as a result of which form the Polynucleotide Binding Agent (herein "PBA") binding site. Selected transcripts and other target polynucleotides can be knocked out using a PBA, which means that the activity or level of the target polynucleotide is diminished or abolished.

A preferred embodiment of the invention provides a method for modulating gene expression comprising the steps of: selecting a polynucleotide binding agent binding site and polynucleotide binding agent; contacting an organism with the binding site and binding agent; and detecting modulation of gene expression. It is preferred that after the contacting step the binding site and binding agent enter the cell and contact an RNA target. It is further preferred that the contacting step comprises having the binding site base pair with an RNA target molecule. It is preferred in any method of the invention comprising a contacting step that such step further comprise the step that the PBA binding site and PBA each enter the cell and contact an RNA target or DNA target, and also are of low toxicity or non-toxic to the host cell.

Any method useful to select or make a polynucleotide that binds specifically to a PBA may be used by the skilled artisan to select or make a PBA binding site. Preferred methods for making or selecting a PBA binding site include, but are not limited to, SELEX, polynucleotide binding assays. Using any of these methods the skilled artisan can make a polynucleotide that binds specifically to a PBA of the invention. Once this polynucleotide is made, flanking sequences complementary to a target polynucleotide are selected. These flanking sequences are added to the PBA-specific polynucleotide to make a polynucleotide that binds specifically to both a target polynucleotide and a PBA. The skilled artisan may use any polynucleotide as a target polynucleotide in which a structural or functional alteration is deemed desirable. For example, the target polynucleotide may be a gene or messenger RNA the expression of which is desired to be altered, such as by gene expression modulation. Other examples of polynucleotide targets are provided elsewhere herein. The methods of the invention may be used in lieu of gene knockout technology. Generally, the methods herein are less time consuming than gene knockout technology.

The PBA can be any compound or element. However, it is preferred that the PBA inhibits or abolishes gene expression or is associated with an inhibition or abolition of gene expression once it binds such polynucleotide and a target polynucleotide using with the methods of the invention. It is further preferred that the PBA be non-toxic or of low toxicity to the host cell and be able to penetrate the host cell. Preferred PBAs include, for example, compounds and elements that generate free radicals or other reactive chemical species, such as singlet oxygen, hydroperoxides, hydroxyl radicals, superoxide, and nitric oxide, and photoreactive dyes. Photoreactive dyes and their uses are well known in the art. See, for example, Turro, N. J. *Molecular Photochemistry* W. A. Benjamin, Inc., New York (1967). Such compounds and methods are useful in this invention. Photorreactive dyes and free-radical generating compounds are also commercially available, such as those available from Molecular Probes, Inc.

PBAs particularly useful in the methods of the invention are those which generate or are predicted to generate reactive oxygen species, either intrinsically, once in an appropriate buffer, or following irradiation with EMR. Preferred PBAs of this type are selected from the group consisting of: hypocrellins and hypericin, tetrabromorhodamine 123, Rose Bengal photooxidizing dye, FotoFenton Reagents (such as 2-mercaptopyridine N-oxide), phenanthrolines, spontaneous nitric oxide donors (such as DEANO, spermine NONOate, S-nitrosoglutathione, SNAP, and SIN-1, each which are commercially available from Molecular Probes, Inc.)

FotoFenton 1 and 2-hydroxyacetophenone oxime (FotoFenton 2) are activated by, for example, UV irradiation.

Hydroxyl radical generators are also useful in the methods of the inventions. An example of these compounds includes Fenton's reagent ($Fe^{2+}/H_2O_2$).

Other PBAs provided by the invention and useful in the methods herein are spontaneous nitric oxide donors. Such donors release nitric oxide under physiological conditions.

Particularly preferred PBAs useful in the methods of the invention include malachite green and isosulfan blue derivatives. The nonfluorescent photosensitizer, malachite green, absorbs at long wavelengths (about 630 nm). Photosensitizing action of malachite green can be targeted to polynucleotides via polynucleotide aptamers disclosed herein. Localization due to targeting of a target polynucleotide by the malachite green aptamer leads to localized production of hydroxyl radicals upon irradiation of the malachite green at a wavelength of about 630 nm. Isosulfan blue is structurally related to malachite green and exhibits significant long-wavelength absorbance. It shows an extinction coefficient of about 110,000 cm-1M-1 at 631 nm in methanol. Reactive sulfonyl chloride of isosulfan blue is commercially available (Molecular Probes, Inc.).

A preferred method for modulating gene expression comprises the steps of: selecting a polynucleotide binding agent binding site and polynucleotide binding agent; contacting an organism with the binding site and binding agent; irradiating the binding agent with electromagnetic radiation; and detecting modulation of gene expression. The electomagnetic radiation includes but is not limited to visible light, particularly blue green and red light, UV light, infrared light, beta particles, X-rays, and gamma rays.

Another preferred method is provided wherein the polynucleotide binding agent is malachite green and the electromagnetic radiation has a wavelength of about 630 nanometers (herein "nm").

The invention also provides a method wherein the modulation of gene expression is lowering or inhibiting gene expression. In order to follow the chemical and physical action of PBAs of the invention, such as their effect on modulation of gene expression, it is useful to use chemical probes and/or gene expression reporter. For instance, singlet oxygen probes allow for the detection of reactive oxygen species. Such detection provides the skilled artisan with a way to detect whether such species are present when any given PBA is used, prior to binding or once bound to its PBA binding site and/or its target polynucleotide. Fluorescent and nonfluorescent compounds useful as probes to detect singlet oxygen include, for example, trans-1-(2'-methoxyvinyl) pyrene (chemiluminescent), anthracene-9,10-dipropionic acid, naphthalene- 1,4-dipropionic acid, 1,3-diphenylisobenzofuran, rubrene, 9,10-diphenylanthracene, and trans-1-(2'-methoxyvinyl)pyrene. Other probes useful for other reactive chemical species are well known in the art and skilled artisans can determine which are the most useful for a given application. Form, example, there are probes for hydroperoxides, hydroxyl radicals, superoxide, and nitric oxide.

Reporter genes may also be used to follow the chemical and physical action of PBAs of the invention, such as, for example, their effect on gene expresion. Examples of such reporter genes include, for example, those well known in the art for qualitatively an/or quantitatively detecting changes in gene expression, such as, beta-galactosidase, luciferase, galactokinase, chloramphenicol acetyl transferase, xanthine-guanine phosphoribosyl transferase, among others.

PBA binding sites may be made or selected for PBA binding using many well known methods. A preferred method for making RNA aptamers that bind PBAs is SELEX. One the RNA is made DNAs may also be made from this aptamer using standard techniques. For example an aptamer may be reverse transcribed, ligated into an vector and replicated in a host cell. Flanking sequences may be a stretch of nucleotides of any length, that are complementary to a polynucleotide sequence of the target polynucleotide. Flanking sequences may be interrupted by nucleotides that are not complementary to the target sequence, and may also comprise nucleotides extending from their 5' and/ or 3' termini.

Preferred PBA binding sites of the invention comprise two flanking sequences, one at the 5' side of the binding site and one at the 3' side of the binding site, and have the general formula:

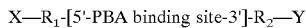

wherein, at -the 5' end of the molecule, X is hydrogen, nucleic acid residue, or modified nucleic acid residue, and at the 3' end of the molecule, Y is hydrogen, a metal, nucleic acid residue, or modified nucleic acid residue, $R_1$ and $R_2$ is any nucleic acid residue, and n is an integer between 1 and 100. Any stretch of nucleic acid residues denoted by either R group, where R is greater than 1, may be either a heteropolymer or a homopolymer, preferably a heteropolymer.

It is preferred that $R_1$ and $R_2$ be between about 5 and 50 nucleotides long. It is more preferred that $R_1$ and $R_2$ be between about 10 and 30 nucleotides long. It is most preferred that $R_1$ and $R_2$ be between about 15 and 20 nucleotides long. A PBA may also binding site comprise a single flanking sequence. Examples of PBA binding sites include but are not limited to SEQ ID NO:1 and SEQ ID NO:2.

Using the methods described herein, aptamers may be raised to phenanthrolines. The bromoacetamide or iodoacetamide of 1,10-phenanthroline to thiol-containing ligands may be used to afford metal-binding properties to this complexing agent. For example, the covalent copper-phenanthroline complex of oligonucleotides or nucleic acid-binding molecules combined with hydrogen peroxide selectively cleaves DNA or RNA (*Biochemistry* 29, 8447 (1990); *J Am Chem Soc* 109, 1990 (1987)). A target polynucleotide may in this way be cleaved upon the addition of metal specific for the chosen phenanthroline.

Other preferred PBAs include, for example compounds and elements that form stable complexes with the PBA binding site and/or the PBA-binding site and the target polynucleotide. Coordination complexes formed by the PBA binding site and PBA are preferred. The invention also provides binding sites selected from the group consisting of a site that: binds a metal ion, creates a coordination complex with a metal ion or other atom or molecule, and is an iron response element. The iron response element (herein "IRE") has been described in the art. The IRE motif may be constructed with selected flanking sequences. An example of a use for this IRE-based PBA binding site is as follows. A cell or composition in which the skilled artisan desires to inhibit target gene expression is contacted by iron ions and an IRE-based PBA binding site, like the one describe above. Gene expression will thereby be inhibited. FIG. 1 (top panel) illustrates an example or a malachite green binding aptamer and FIG. 1 (lower panel) shows an example of a preferred PBA binding site for malachite green.

Also provided is a method wherein the PBA is selected from the group consisting of: malachite green, an iron salt, an organo-iron compound, an iron coordination compound, an iron ion (ferrous or ferric) or a radioactive iron radionuclide. Such PBAs will be particularly useful with PBA binding sites comprising an IRE.

A further preferred method is hereby provided wherein the contacting step also comprises contacting the binding site agent with a metal ion, metal salt or metal oxide.

Target polynucleotides of the invention may be any polynucleotide, particularly ones in which the skilled artisan wants to alter the structure and/or activity or the polynucleotide. Most preferred target polynucleotides are DNAs and RNAs that perform a biological function, such as catalytic RNAs, expressed genes, genes capable of expression, mRNAs, snRNP RNAs and hnRNAs. Target polynucleotides of the invention may also be DNA and RNA from pathogens, including, for example, fungi, such as Coccidioides, Saccharomyces, and Candida; protozoa, such as Giardia; prokaryotes, such as Gram positive organisms, Streptococcus, Staphylococcus, Gram negative organisms, *E. coli*, *K. pnetimoniae*, and *Legionella pneumophila*, staphylococci, streptococci; viroids, virusoids and viruses, such as HIV 1 and 2, HSV 1 and 2, HAV, HBV, and HCV and the delta agent.

A preferred method of the invention is directed to altering the structure of a polynucleotide comprising the steps of: selecting a polynucleotide binding agent binding site and polynucleotide binding agent; contacting a polynucleotide with the binding site and binding agent; and detecting an alteration in the structure of the polynucleotide. Another preferred method is provided wherein the alteration in the structure is a cleavage of the polynucleotide phosphate backbone, perferably occurring via a chemical or physical effect of the PBA, such as, metal ion scission, beta particle scission, gamma scission, or free radical binding.

In preferred embodiments of the methods and compositions of the invention, the microbes are pathogenic to humans and/or non-human vertebrates, particularly non-human mammals. Examples of organisms useful in or with the methods and compositions of the invention include, for example, a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi*, Bordetella, *Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigelia dysenterii, Shigella flexneri, Pseudomonas aeruginosa, Franscisella tularensis, Brucella abortis, Bacillus anthracis,*

Bacillus cereus, Clostridium perfringens, Clostridium tetani, Clostridium botulinum, Treponema pallidum, Rickettsia rickettsii and Chlamydia trachomitis, (ii) an archaeon, including but not limited to Achaebacter, and (iii) a unicellular or filamentous eukaryote, including but not limited to, a protozoan, a fungus, a member of the genus Saccharomyces, Kluveromyces, or Candida, Coccidiodes, Histoplasma, Cryptococcus and Paracoccidioldes.

In another preferred embodiment a target polynucleotide comprises a portion of the functional PBA binding site. It is particularly preferred that such portion of the target polynucleotides be between the sequences that are complementary to the flanking sequences of the PBA binding site. FIG. 1 (bottom panel) provides an example of such a preferred embodiment where a PBA binding site and a portion of the target polynucleotide bind malachite green (SEQ ID NO:2).

It is preferred that the polynucleotide that forms all or part of the PBA is an RNA, DNA or an RNA-DNA hybrid. It is also preferred that this polynucleotide be provided in trans in the methods of the invention, but it may be provided in cis.

In view of the methods and compounds provided by the claimed invention, skilled artisans can readily invisage kits comprising such compounds, particularly in forms or packs that are useful for use with such methods.

A preferred kit provided by the invention comprises at least one compartment containing an isolated PBA binding site and a PBA. It is preferred that such containers be rigid and fabricated of plastic or glass. However, they may also be configured as blister packs.

A further preferred kit comprises the PBA selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donors, DEANO, spermine NONOate, S-nitrosoglutathione, SNAP, SIN-1, M-7904, 2-hydroxyacetophenone oxime and Fenton's reagent. A particularly preferred kit comprises the malachite green packaged with a PBA binding site for malachite green.

Each reference cited herein is hereby incorporated by reference in its entirety. Moreover, each patent application to which this application claims priority is hereby incorporated by reference in its entirety.

What is claimed is:

1. A method for modulating gene expression comprising the steps of:
   selecting a polynucleotide binding agent binding site and polynucleotide binding agent;
   contacting an organism with said binding site and binding agent; and
   detecting modulation of gene expression, wherein said polynucleotide binding agent is selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donor, DEANO, spermine NONOate, S-nitrosoglutathione, SNAP, SIN-1, M-7904, 2-hydroxyacetophenone oxime and Fenton's reagent.

2. The method of claim 1 wherein said modulation of gene expression is lowering of gene expression.

3. The method of claim 1 wherein said binding site is selected from the group consisting of: malachite green aptamer, and an iron response element.

4. A method for altering the structure of a polynucleotide comprising the steps of:
   selecting a polynucleotide binding agent binding site and polynucleotide binding agent;
   contacting a polynucleotide with said binding site and binding agent; and
   detecting an alteration in the structure of said polynucleotide, wherein said polynucleotide binding agent is selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donor, DEANO, spermine NONOate, S-nitrosoglutathione, SNAP, SIN-1, M-7904, 2-hydroxyacetophenone oxime and Fenton's reagent.

5. The method of claim 4 wherein said alteration in the structure is a cleavage of the polynucleotide phosphate backbone.

6. The method of claim 4 wherein said binding site is selected from the group consisting of: malachite green aptamer, and an iron response element.

7. A method for modulating the function of a polynucleotide comprising the steps of:
   selecting a polynucleotide binding agent binding site and polynucleotide binding agent;
   contacting a polynucleotide with said binding site and binding agent; and
   detecting modulation of said function, wherein said polynucleotide binding agent is selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donor, DEANO, spermine NONOate, S-nitrosoglutathione, SNAP, SIN-1, M-7904, 2-hydroxyacetophenone oxime and Fenton's reagent.

8. A method for modulating gene expression comprising the steps of:
   selecting a polynucleotide binding agent binding site and polynucleotide binding agent;
   contacting an organism with said binding site and binding agent irradiating said binding agent with electromagnetic radiation; and
   selected from the group of gene expression, wherein said polynucleotide binding agent is generating from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donor, DEANO, spermine NONOate, S-nitrosoglutathione, SNAP, SIN-1, M-7904, 2-hydroxyacetophenone oxime and Fenton's reagent.

9. The method of claim 8 wherein said binding site is selected from the group consisting of: malachite green aptamer, an aptamer to a photoreactive dye, and an aptamer to a free radical generating compound.

10. The method of claim 8 wherein said contacting step also comprises contacting said binding site agent with a metal ion, metal salt or metal oxide.

11. The method of claim 8 wherein said polynucleotide binding agent is malachite green and said electromagnetic radiation has a wavelength of about 630 nanometers.

12. A kit comprising at least one compartment containing an isolated polynucleotide binding agent binding site and a polynucleotide binding agent, wherein said polynucleotide binding agent is selected from the group consisting of: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donor, DEANO, spermine NONOate, S-nitrosoglutathione, SNAP, SIN-1, M-7904, 2-hydroxyacetophenone oxime and Fenton's reagent.

13. A method for modulating gene expression comprising the steps of:
   selecting a polynucleotide binding agent binding site and polynucleotide binding agent;
   contacting an organism with said binding site and binding agent; and
   detecting modulation of gene expression, wherein said binding site is selected from the group consisting of that bind: malachite green, a photoreactive dye, a free radical generating compound, an iron salt, an iron ion, a radioactive iron radionuclide, isofuran blue, an isosulfan blue derivative, reactive sulfonyl chloride of isosulfan blue, hypocrellins and hypericin, tetrabromorhodamine, Rose Bengal photooxidizing dye, a FotoFenton reagent, 2-mercaptopyridine N-oxide, phenanthrolines, a spontaneous nitric oxide donor, DEANO, spermine NONOate, S-nitrosoglutathione, SNAP, SIN-1, M-7904, 2-hydroxyacetophenone oxime or Fenton's reagent.

* * * * *